(12) United States Patent
Al-Qbandi et al.

(10) Patent No.: US 8,419,767 B2
(45) Date of Patent: Apr. 16, 2013

(54) STEERABLE ATRIAL SEPTAL OCCLUDER IMPLANTATION DEVICE WITH FLEXIBLE NECK

(76) Inventors: Mustafa H. Al-Qbandi, Shuhadaa (KW); Omar A. Al-Bannai, Aladailiya (KW); Fawzi Q. Behbehani, Abdullah Mubarak (KW)

( * ) Notice: Subject to any disclaimer, the term of this patent is extended or adjusted under 35 U.S.C. 154(b) by 250 days.

(21) Appl. No.: 12/773,114

(22) Filed: May 4, 2010

(65) Prior Publication Data

US 2011/0276086 A1 Nov. 10, 2011

(51) Int. Cl.
- *A61B 17/03* (2006.01)
- *A61B 1/00* (2006.01)
- *A61M 25/01* (2006.01)
- *A61M 31/00* (2006.01)

(52) U.S. Cl.
USPC ........ 606/213; 600/141; 600/146; 604/95.01; 604/523

(58) Field of Classification Search .................. 606/213; 600/139–142, 146, 149; 604/95.01, 95.04, 604/523, 528, 532
See application file for complete search history.

(56) References Cited

U.S. PATENT DOCUMENTS

| | | | |
|---|---|---|---|
| 4,108,211 A | 8/1978 | Tanaka | |
| 4,473,077 A | 9/1984 | Noiles | |
| 5,042,707 A | 8/1991 | Taheri | |
| 5,297,443 A * | 3/1994 | Wentz | 74/490.04 |
| 5,348,259 A | 9/1994 | Blanco | |
| 5,704,534 A | 1/1998 | Huitema | |
| 5,749,828 A | 5/1998 | Solomon | |
| 5,944,738 A * | 8/1999 | Amplatz et al. | 606/213 |
| 6,482,224 B1 | 11/2002 | Michler | |
| 7,087,072 B2 | 8/2006 | Marino | |
| 2005/0085693 A1* | 4/2005 | Belson et al. | 600/146 |
| 2005/0197536 A1* | 9/2005 | Banik et al. | 600/179 |
| 2008/0045803 A1* | 2/2008 | Williams et al. | 600/204 |

* cited by examiner

*Primary Examiner* — Corrine M McDermott
*Assistant Examiner* — Shaun L David
(74) *Attorney, Agent, or Firm* — Richard C. Litman

(57) ABSTRACT

An atrial septal occluder device for repairing an atrial septal defect in a human heart includes an elongated catheter for insertion into and moved along a blood vessel and into the heart of a patient. The catheter includes a head portion, a tail portion and a neck portion between the head and tail portions. The neck portion is about 1 cm in length and 2 to 4 mm in diameter. The device also includes an Amplatzer ASO removably fixed to the head of the device and a moveable neck portion for positioning the ASO with respect to the ASD and an activator for closing the ASO over the ASD from outside of the patient's body.

2 Claims, 7 Drawing Sheets

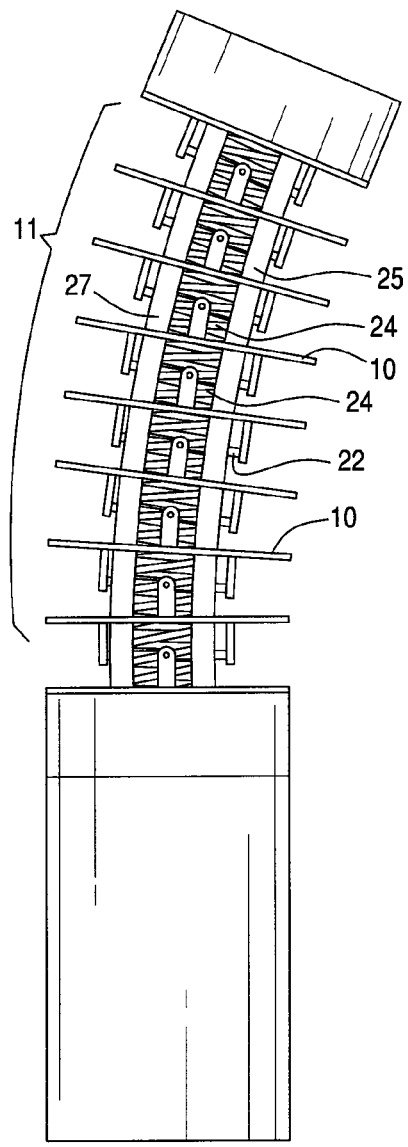
FIG. 12
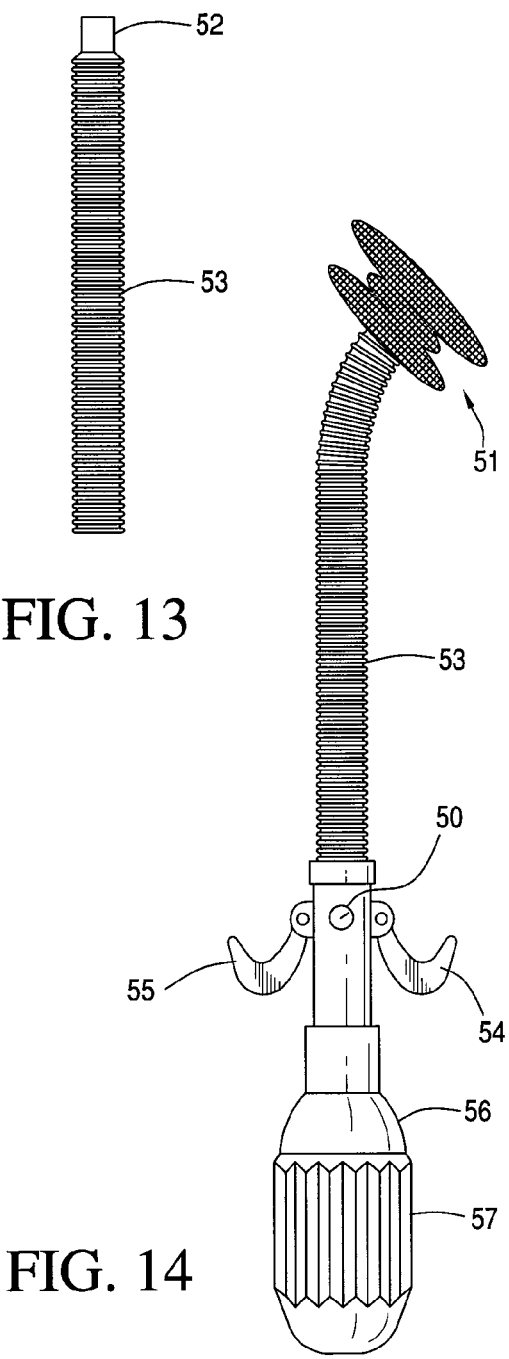
FIG. 13
FIG. 14

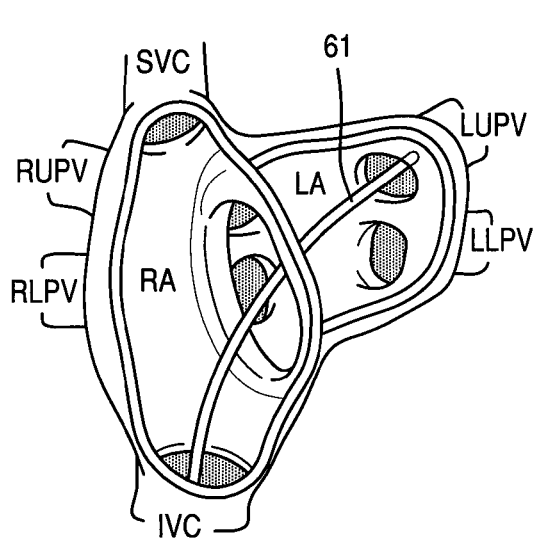
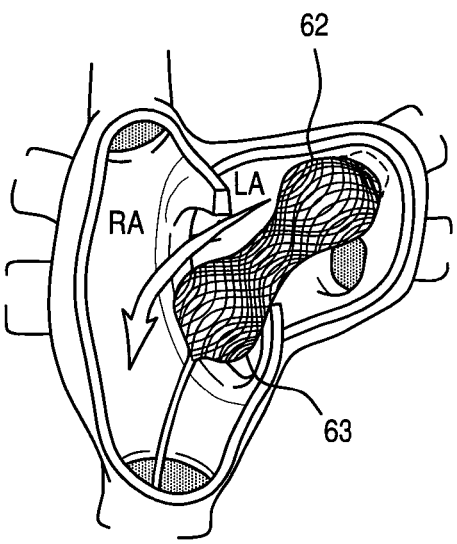
FIG. 15a  FIG. 15b
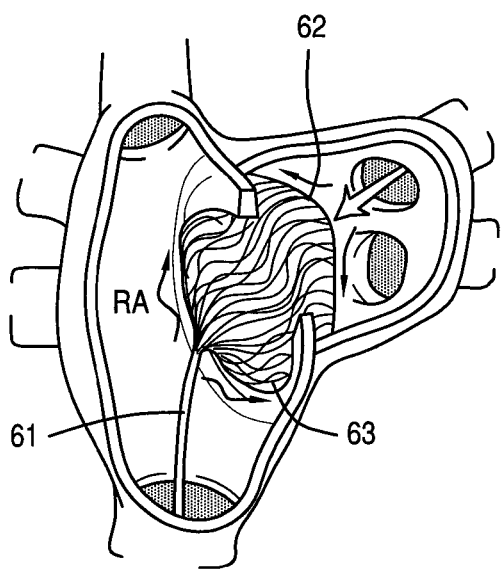
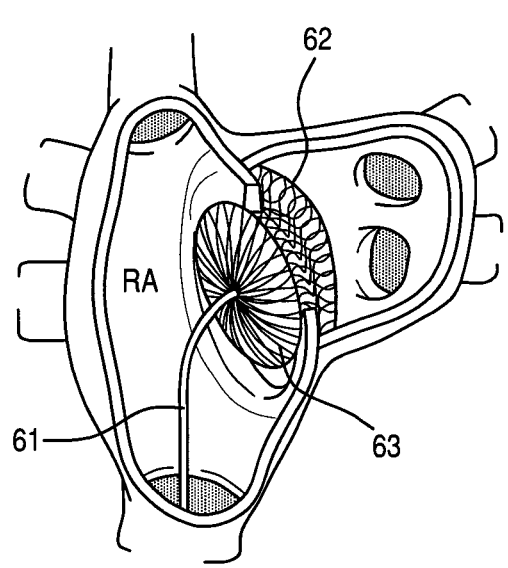
FIG. 15c  FIG. 15d

STEERABLE ATRIAL SEPTAL OCCLUDER IMPLANTATION DEVICE WITH FLEXIBLE NECK

FIELD OF THE INVENTION

This invention relates to an atrial septal occluder device and method, and more particularly to medical cardiac catheterization that includes a modification to an Amplatzer cable that helps to orient the Amplatzer device to be parallel to the plane of the atrial septal.

BACKGROUND FOR THE INVENTION

Atrial septal defects (ASDs) account for 10% of all congenital heart lesions and are commonly diagnosed in adulthood. Closure of these defects is indicated to prevent the development of reduced exercise tolerance, atrial arrhythmias, congestive heart failure, and pulmonary hypertension. Catheter device closure has been in use for 20 years and is as effective as surgery but with less morbidity. Atrial septal defects (ASDs) are among the most common congenital heart defects, with approximately 18% of defects 4 mm or greater requiring intervention. Additionally, natural history studies have shown that ASDs with diameters of 8-10 mm rarely close and usually require intervention. In past years, surgery was the only option for repair of defects with larger diameters, but since the first reported trans-catheter closure of ASD by King in 1976, efforts are leading to the closure of such defects by trans-catheter techniques.

The interventional cardiologist looks at ASDs as either simple or complex. Those simple can be closed easily by conventional devices without complications. However, the complex ones can either end by fixing the defect in the cardiac catheterization laboratory or in the operating room by the surgeon.

The complex ASD anatomy was arbitrarily defined as ASDs with stretched diameters larger than 26 mm with a deficient (<4 mm) rim, two separate ASDs with a distance greater than 7 mm, fenestrated atrial septum or redundant and hypermobile (>10 mm) atrial septum.

Complex anatomy ASD that may require the use of the present invention include:
1. Large ASD secundum
2. Deficient anterosuperior rim ASD
3. Multiple or fenestrated ASD
4. Deficient posteroinferior rim ASD
5. Aneurysmal atrial septum
6. Combination of the above Large Defects:

One complex anatomy of ASDs is simply the size of the defect even with adequate rims. A large ASD has been defined as an ASD with a stretched diameter>26 mm. A similar definition was used by other workers in this field. Although it seems like a simple problem, the questions would be how large a device could be used to close such a defect, whether or not the left atrium would accommodate such device and whether such a large device would encroach on other intra-cardiac structures (e.g., mitral valve) or obstruct blood flow (e.g., vena cavae or pulmonary veins). As pointed out recently, large defects are likely to be associated with deficient posterior-inferior rim, which makes the device implantation even more difficult.

Deficient Anterosuperior Rim:

A deficient anterosuperior rim is frequently encountered with large ASDs and indeed in our own personal experience most patients we attempt to occlude with various devices were found to have a deficient anterior superior rim. In one study it is the deficient inferior rim that was found to be associated with unsuccessful Amplatzer® implantations. An Amplatzer septal occluder, (AGA Medical Corp, Golden Valley Minn. is a self-centering device that has been successfully used in clinical trials. With deficient anterior rim, the disks of the Amplatzer device straddle the ascending aorta. With other double disk devices the left atrial disk sits on the back of the aorta. Initial reports of erosion of the aortic wall by the ASO with development of aorta-to-right atrium or aorta-to-left atrium fistulae led to the recommendation of over-sizing (i.e. using a device size 4 mm larger than the measured stretched diameter) the implanted device in large defects with deficient anterior superior rim to ensure the device disks straddle and remain flared around the ascending aorta to prevent discrete areas of pressure where erosion may occur. When over-sizing the device, care has to be taken not to interfere with surrounding intra-cardiac structures.

However, the difficulty in deploying the atrial septal occluder ASO in patients with deficient anterior superior rim is that the left atrial disk tends to become perpendicular to the atrial septum leading to prolapse of the left disk into the right atrium, representing a challenging difficulty.

Multiple or Fenestrated Defects.

These represent another complex anatomy of the ASD which may be successfully closed using different techniques or devices. One approach reported the use of balloon atrial septostomy to create a single large defect that could then be closed with a single large ASO device. We are not in favor of using such a technique. Szkutnik et al. reported a technique, which has been used in many institutions and that is using a single ASO device deployed in the larger defect to occlude two or more smaller defects. In their series, a smaller defect less than 7 mm distance from the larger defect had a 100% closure rate at one-month follow-up. Deploying the device in the larger defect may decrease the distance between the two defects or even compress the smaller defect. They found that if the distance between the two defects is >7 mm, a residual left to right shunt will persist.

Deficient Posteroinferior Rim:

Closure of a large ASD with deficient or absent posteroinferior (PI) rim continues to be a challenge. An insufficient number of cases with deficient PI rims were reported and makes it more difficult to have a solid consensus. Pedra et al. mentioned one case with deficient anterior rim and a floppy, thin and hyper mobile posterior rim that was not a good candidate for device closure. Du et al. reported patients with deficient rims, of which 3 patients had deficient inferior or posterior rims. Two patients had 2 mm of posterior rim and the third had a 4 mm posterior rim. These 3 patients were successfully closed. Yet, the number of cases is too small to make a generalized conclusion. Lack of detailed anatomical description of the deficient rims and surrounding rims and defects in most reported studies adds to difficulty in drawing useful conclusions. Mathewson et al. defined absent PI rim as a rim<3 mm. As the difference in radius length between right and left atrial disks of the ASO is 2-3 mm, a rim<3 mm will not allow both disks to hang on both sides of the rim. They found that defects with absent PI rim tend to be larger in diameter. They concluded that, although a stable ASO deployment is possible, these defects are more liable for complications such as pulmonary vein or IVC obstruction, encroachment onto the anterior mitral leaflet, or frank embolization.

Aneurysmal Atrial Septum:

Septal aneurysms with single or multiple defects represent a different kind of complex anatomy of the ASD. Such anatomy is better dealt with devices that don't rely on stenting mechanism within the defect to achieve stabilization in the septum. Patch or double disc type of devices such as the COD buttoned device, the Helex, the CardioSeal or the more recent Amplatzer cribriform are more appropriate choices to close such defects.

In conclusion, most cases of complex anatomy of secundum atrial septal defects can be closed successfully either by using traditional or special techniques or devices. Defects with deficient or absent posteroinferior rim continue to form a challenging task for most interventional cardiologists.

In essence the problem associated with an Amplatzer septal occluder devices (ASOD) which is the most common technique used to close atrial septal defects is that the cable has limited maneuverability (rotational steerage) inside a heart chamber. This is more obvious in cases of large atrial septal defectes with deficient rims.

The solution is to modify the device so that it can be steered enough to orient the device to be generally parallel to the plane of the atrial septum. Thus, Applicant's have modified the neck (distal segment) of the Amplatzer cable and refer to it as COBRAX because it moves like a cobra snake.

Methods to Prevent Amplatzer Disk Prolapse:

One method suggested to prevent disk prolapse when rim deficiencies or atrial dimensions restrict device orientation is to withdraw a partially deployed device from the mouth of the right upper pulmonary vein, in contact with the posterior superior septum, in an attempt to maintain the device parallel to the atrial septum as it is deployed. This maneuver can avoid rotation of the left atrial disk. Another method that has also been successful is engagement of the left upper pulmonary vein with the left atrial disk and deployment of the right atrial disk. This maneuver relies on induced tension to pull the left atrial disk toward the septum once the right atrial disk is engaged. Another technique is the use of a special braided reinforced sheath with two curves at its end (Hausdorf sheath, Cook, Bloomington, Ind.). The sheath always aligns the left atrial disk parallel to the septum, avoiding prolapse of the disk through the defect. A large experience with this catheter, however, is lacking. However, a disadvantage of the Hausdorf sheath is its bulky shape, making it difficult to maneuver through the inferior vena cava and a small right atrium. After attempting the standard technique of deployment, if prolapse occurred two or three times, then we attempted the right upper pulmonary vein approach followed by the left pulmonary vein approach. Caution is advised when recurrent rotation of the sheath is required, as it may inadvertently unscrew the device. To prevent this, the delivery wire must be rotated with the device. High-resolution fluoroscopic magnification of the junction between the microscrew of the device and the screw in the cable can ensure the connection windings are appropriate with no gap between the two. Excessive manipulation within the left atrium itself may be hazardous with the potential for perforation. The techniques used for closure of large defects are at the high end of the learning curve. Large device implants are feasible with views from ICE when it is essential to have high-quality imaging to position the implant reliably. The use of ICE catheters may improve visualization of the inferior rim compared to TEE. A new approach with use of a second sheath or sizing balloon to stabilize the inferior aspect of the retention disc while deploying the right atrial disc has been reported as a useful method for complex ASD closures. Yet, these maneuvers necessitate an additional large venous access on the contralateral femoral site, potentially increasing the risk of vascular access complications. Finally, a modified, shortened Mullins-type delivery sheath with a bevel at its inner curvature may facilitate deployment of an ASO in complex, large secundum ASDs with deficient rims. A modified Agilis sheath has also been used to overcome the difficulties in closing complex ASD's.

BRIEF SUMMARY OF THE INVENTION

In essence the present invention contemplates a steerable atrial septal occlude device for repairing an atrial septal defect in a human heart. The device includes an elongated catheter that is adapted to be inserted into and moved along a blood vessel and into the heart of a patient. While a distal end of the catheter is inserted into the heart, a proximal end is adapted to remain outside of the patient's body. The catheter includes a head portion at the distal end, a main or tail portion and a neck portion disposed between the head portion and the tail portion. The neck portion is about 1cm in length and 2mm in diameter which is the same as the diameter of the head and tail portion. The device also includes an atrial septal occluder such as an Amplatzer ® ASO removably fixed to the head portion of the catheter. Means are provided for positioning the atrial septal occlude with respect to an atrial septal defect by changing the curvature of the neck portion from the proximal end of the catheter. In addition, the device includes means for closing the atrial septal occlude over an atrial septal defect from the proximal end of the catheter and means for separating the atrial septal occlude from the head portion of the catheter.

The device in accordance with the present invention looks like a chain which is 1 cm in length that is added to a standard Amplatzer ® cable and that has the ability to freely move the device inside the heart chamber. The diameter of the Cobrax portion of the cable is 2 mm and can be bent up to 90°. The Cobrax contains steel discs, steel springs, steel universal joints and two steel pulling rods. Each disc is attached to each other vertically as illustrated.

The invention will now be described in connection with the following drawings wherein like numbers have been used to identify like parts.

DESCRIPTION OF THE DRAWINGS

⊕ Means the top of the object
⊖ Means the bottom of the object
⊙ Means the front of the object

FIG. 12 is a side view of a catheter including a curved neck portion in accordance with the present invention;

FIG. 13 is a side elevational view of a main body portion of a catheter without the neck portion;

FIG. 14 is a side elevational view of a catheter assembly including a handle, control levers, release mechanism and a neck portion and Amplatzer AOL;

FIG. 15 (a-d) illustrates a distal portion of a catheter in repairing an ASD with an Amplatzer ASO.

DESCRIPTION OF THE PREFERRED EMBODIMENTS OF THE INVENTION

Figure 1:
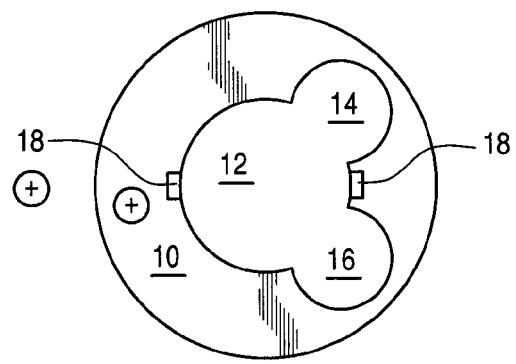
FIG. 1 is a top or plan view of a disc as used in the present invention.

As illustrated in FIGS. 1-4, a neck portion 11 of an atrial septal occluder in accordance with the present invention includes a plurality of stainless steel discs 10 having a generally circular cross section with a 2-4 mm diameter and that includes a plurality of connected segments. Each of the discs 10 defines three overlapping passageways, 12, 14 and 16. A first or central passageway 12 includes an upper coil spring portion extending through the center of the disc and held in place by upper and lower cross members that act as universal joints by being rotatably mounted in a pair of upwardly extending hinge members 18 and by a pair of downwardly extending hinge members 20.

Figure 2:
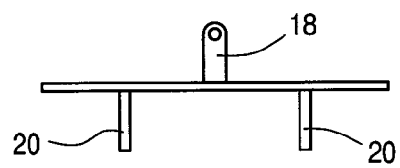
FIG. 2 is a side view of the left side of the disc shown in FIG. 1.

As illustrated more clearly in FIG. 2, each of the discs 10 include a pair of upperwardly extending hinge members 18 and a pair of downwardly extending hinge members 20 on the opposite side of the disc 10.

As shown in FIG. 1, each of the discs 10 includes a left pulling rod opening 14 and a right pulling rod opening 16 for bending the neck portion 11 to the left or to the right for positioning the atrial septal occluder with regard to a atrial septal defect. In a preferred embodiment of the invention, the position of the atrial septal occlude is linked to the neck portion which is approximately 1 centimeter (cm) in length and used to position the ASO with the patient's heart.

Figure 3:
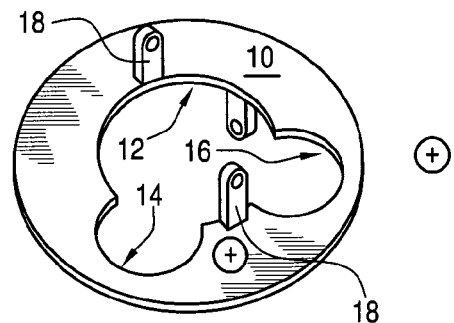
FIG. 3 is a perspective view of the disc as shown in FIG. 1.
Figure 4:
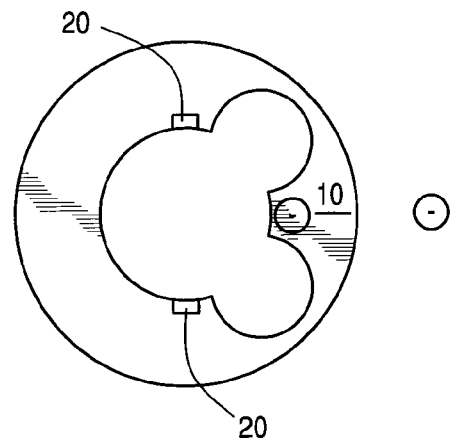
FIG. 4 the underside of the disc shown in FIGS. 1-3.
Figure 5:
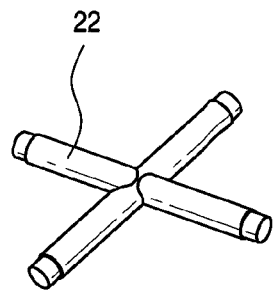
FIG. 5 is a perspective view of a universal joint including a crossbar that fits into two hinge holders on opposite sides of a disc.
Figure 6:
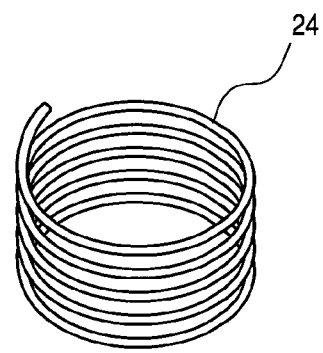
FIG. 6 is a perspective view of a coil spring as used in a neck portion of a catheter in accordance with the present invention.
Figure 7:
FIG. 7 is front elevational view of a head portion as used for attaching an Amplatzer AOL to a neck portion of a catheter in accordance with the present invention.
Figure 8:
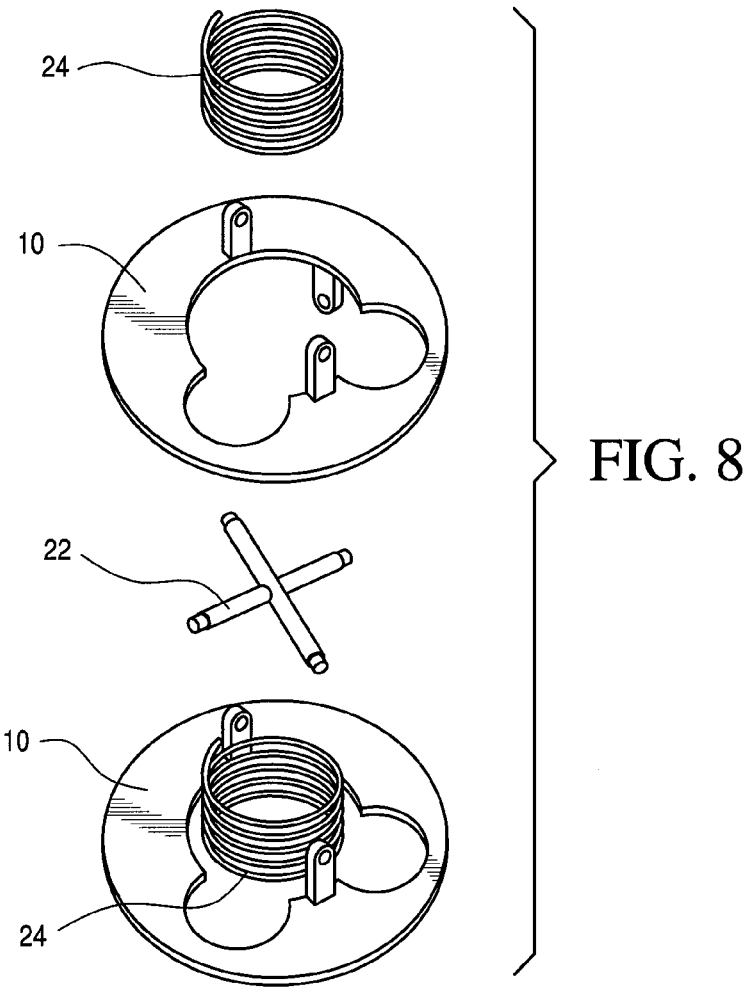
FIG. 8 is a exploded view of two disc, springs and universal joint as used in a neck portion of a catheter in accordance with the present invention.
Figure 9:
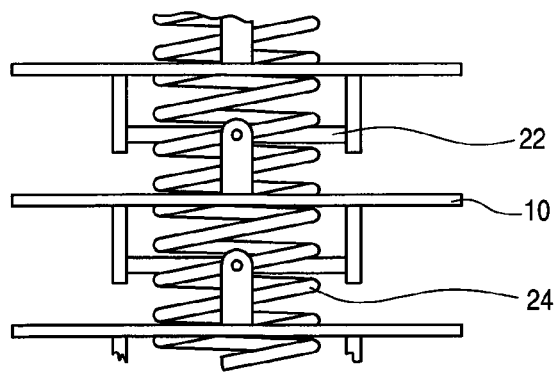
FIG. 9 is a side elevational view of a spring, disc, crossbar and universal joint in accordance with the present invention.
Figure 10:
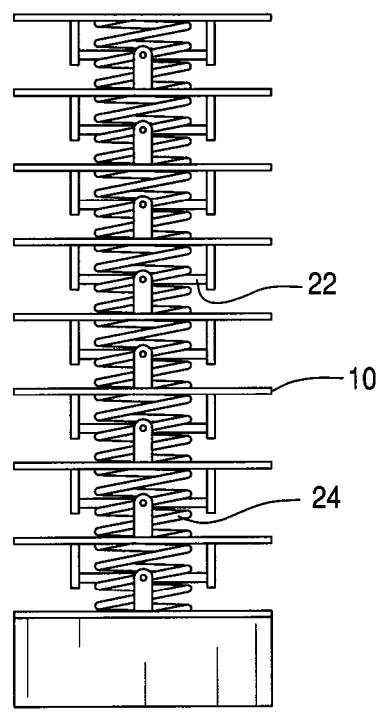
FIG. 10 is a side elevational view of a disc assembly as used in a neck portion of a catheter in accordance with the present invention.
Figure 11:
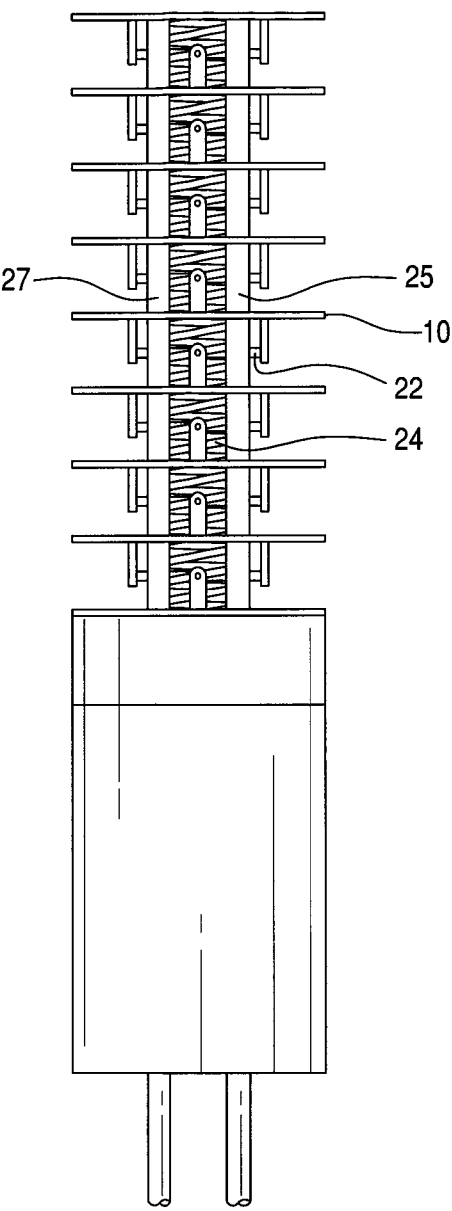
FIG. 11 is a side elevational view of the neck portion of the disc assembly shown in FIG. 10 but including a pair of control rods or wires attached to the main body of a catheter.
Figure 16A:
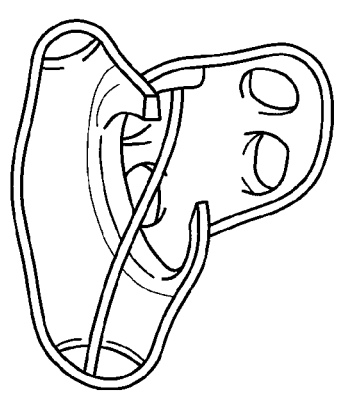
FIG. 16 (a-e) illustrates another technique for closing an ASD with an Amplatzer ASO in accordance with the present invention.
Figure 16B:
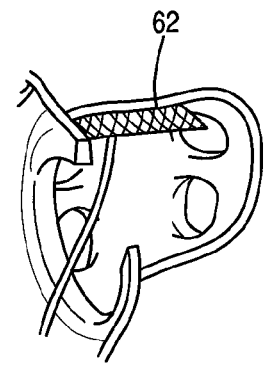
Figure 16C:
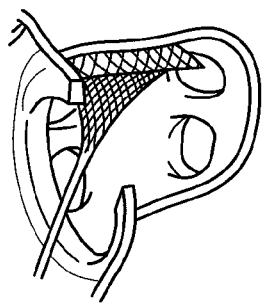
Figure 16D:
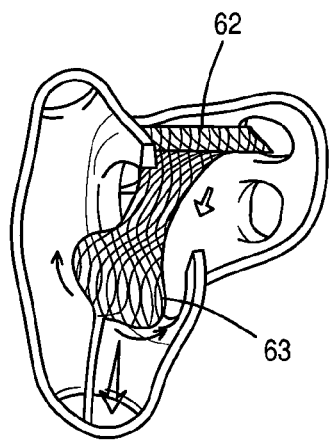
Figure 16E:
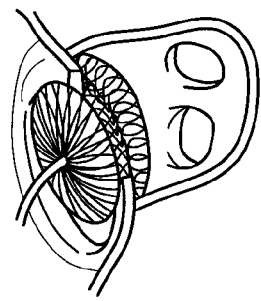

FIG. 3 illustrates a disc from an upper angle while FIG. 4 shows the same disc looking upward from the bottom of the disc. As shown in FIG. 5 a universal joint 22 is disposed between alternate segments while a coil spring 24 is shown in FIG. 6 and the head 26 of the atrial septal occluder is illustrated in FIG. 7. The septal occlude device is attached to the neck portion 11 and extends for a length of about 70 cm.

Figure 12 shows the neck portion including pulling rods or wires 25 and 27. As shown in FIG. 12 the pulling rods or wires 25 and 27 extend beyond the neck portion 11 to an external control on the portion of the catheter that extends outside of a patient's body.

The movement of the neck portion is shown in FIGS. 13 and 14.

An atrial septal occluder device in accordance with the present invention is shown more clearly in FIG. 14. As shown, a complete "cobrax" device includes an amplatzer atrial septal occluder 51 that is connected onto the head portion 52 of a cable 53. The neck portion 11 of the cable can be positioned by pulling on a first lever 54 and/or second lever 55 to achieve movement of the head portion by as much as 90°. The length of the cable is about 70 cm which allows the proximal end to extend into a human heart. As shown, the head of the device is bent at about 40°. A latch assembly 50 is disposed between the left and right levers 54 and 55 and is used to fix the angular orientation of the atrial septal occluder. Then when a first and second portion of the occluder are finally positioned, the occluder is unscrewed from the cable by rotating the control portion 57 of the handle 56 and the cable is removed from the patient's vein.

A repair of an atrial septal defect will now be described in connection with FIGS. 15 (a-d). For example, a delivery tip 61 extends into a heart and into the left upper pulmonary vein (see FIG. 15a) and the delivery is partially withdrawn to allow both expandable discs 62 and 63 of an Amplatzer ®ASO to expand simultaneously as shown in FIG. 15b thereby locating expandable discs on each side of an ASD. As the right disc expands, the cable is pushed to the right as shown in FIG. 15c until both expandable discs 62 and 63 are fully expanded with one disc on each side of the ASD (see FIG. 15d) at which time the ASO is released from the tip 61 by being unscrewed therefrom by the control 57 on handle 56.

Another approach for closing a large ASD with an Amplatzer ASO is illustrated in FIGS. 16 a-e. As shown, the top of a delivery tip 61 is positioned close to the left atrial roof (FIG. 16 a) and the first expandable disc is initially deployed as shown in FIGS. 16 a, b, and c. As the second expandable disc 63 starts to open the discs 62 and 63 are pulled to bring the disc 62 into contact with the large ASD as the second expandable disc 63 expands and is pushed against the outer walls of the ASD to sandwich the ASD between the two expandable discs 62 and 63. Then when both discs 62 and 63 are fully expanded with the ASD, sandwiched therebetween, the ASO is released and the delivery tip 61 removed from the Amplatzer ASO and from the patient's vein.

While the invention has been described in connection with its accompanying drawings it should be recognized that changes and modifications may be therein without departing from scope of the appended claims.

What is claimed is:

1. A steerable atrial septal occluder device for repairing an atrial septal defect in a human heart, said device comprising:

an elongated catheter having a distal end adapted to be inserted into and moved along a blood vessel and into a heart of a patient, wherein said distal end is adapted to receive an atrial septal occluder;

the elongated catheter further having a proximal end adapted to remain outside of a patient's body and said catheter including a head portion, a tail portion and a neck portion between said head portion and said tail portion and said neck portion including a plurality of series connected segments disposed between said head portion and said tail portion, wherein said neck portion further includes a plurality of axially aligned discs having a central opening defined by an open and continuous passageway through said plurality of discs, said central opening being defined by three overlapping openings, wherein a first opening has a first size and the remaining two openings have a smaller size, wherein each of said discs includes a pair of upwardly extending elements and a pair of downwardly extending elements;

a plurality of coil springs, wherein each of the plurality of discs is separated by at least one of the plurality of coil springs, the coil springs being sized to conform with the first opening;

two control cables for positioning the atrial septal occluder within a patient's heart, wherein the cables are located within the remaining two openings in the discs;

a universal joint between each of said discs in said neck portion of said elongated catheter, wherein said universal joint includes an X-shaped pair of cross bars for engaging said spring and two ends of said cross bars are rotatably disposed in said upwardly and downwardly extending members;

means including a control mechanism for closing the atrial septal occluder over an atrial septal defect from said proximal end;

means for separating the atrial septal occluder from said head portion of said catheter from said proximal end of said catheter.

2. A steerable atrial septal occluder device for repairing an atrial septal defect in a human heart according to claim 1, in which said central opening defines three overlapping circular cross sections with overlapping peripheries.

* * * * *